United States Patent [19]
Schur

[11] Patent Number: 5,542,930
[45] Date of Patent: Aug. 6, 1996

[54] CATHETER ASSEMBLY

[76] Inventor: Israel Schur, 10 Amsterdam Ave., Apt. 309, New York, N.Y. 10023

[21] Appl. No.: 531,207

[22] Filed: Sep. 19, 1995

Related U.S. Application Data

[63] Continuation-in-part of Ser. No. 369,751, Jan. 1, 1995, abandoned.

[51] Int. Cl.$^6$ ..................................................... A61M 5/00
[52] U.S. Cl. ........................... 604/164; 604/165; 604/161
[58] Field of Search .............................. 604/52, 53, 93, 604/158, 160, 161, 163, 164, 165, 166, 171

[56] References Cited

U.S. PATENT DOCUMENTS

| | | | |
|---|---|---|---|
| 1,527,291 | 2/1925 | Zorraquin. | |
| 3,727,613 | 4/1973 | Sorenson et al. | 128/214.4 |
| 4,013,080 | 3/1977 | Froning | 128/347 |
| 4,230,123 | 10/1980 | Hawkins, Jr. | 128/658 |
| 4,518,383 | 5/1985 | Evans | 604/51 |
| 4,607,868 | 8/1986 | Harvey et al. | 285/332 |
| 4,798,591 | 1/1989 | Okada | 604/164 |
| 4,969,875 | 11/1990 | Ichikawa | 604/164 |
| 5,007,901 | 4/1991 | Shields | 604/110 |
| 5,104,381 | 4/1992 | Gresl et al. | 604/164 |
| 5,129,887 | 7/1992 | Euteneuer et al. | 606/194 |
| 5,133,362 | 7/1992 | Moss | 128/763 |
| 5,176,415 | 1/1993 | Choksi | 185/331 |
| 5,215,529 | 6/1993 | Fields et al. | 604/168 |
| 5,261,887 | 11/1993 | Walker | 604/161 |
| 5,306,272 | 4/1994 | Cohen et al. | 606/1 |
| 5,380,292 | 1/1995 | Wilson | 604/164 |

Primary Examiner—Sam Rimell
Attorney, Agent, or Firm—Fitch, Even, Tabin & Flannery

[57] ABSTRACT

The catheter assembly of the present invention comprises (i) a needle component, (ii) a catheter component mounted on the needle component in a manner that permits relative axial movement between the needle component and the catheter component, and (iii) a rotatable screw means for controlling the relative axial movement between the needle component and the catheter component and for inducing rotational movement to the catheter component. The improved catheter assembly of the invention facilitates the insertion of the catheter component into a vessel of a patient and permits precise control of the relative positions of the components of the assembly to one another. In one application, the invention provides an improved intravenous catheter (I.V. catheter).

27 Claims, 4 Drawing Sheets

CATHETER ASSEMBLY

RELATED APPLICATION

This is a continuation-in-part of U.S. patent application Ser. No. 08/369,751 filed on Jan. 1, 1995, now abandoned.

FIELD OF THE INVENTION

The present invention relates to an improved catheter assembly which facilitates the insertion of the catheter component into a blood vessel or other confined anatomical space of a patient and permits precise control of the relative positions of the components of the assembly to one another. In one application, the invention provides an improved intravenous (I.V.) catheter.

BACKGROUND OF THE INVENTION

Figures 9, 10, 11, 12:
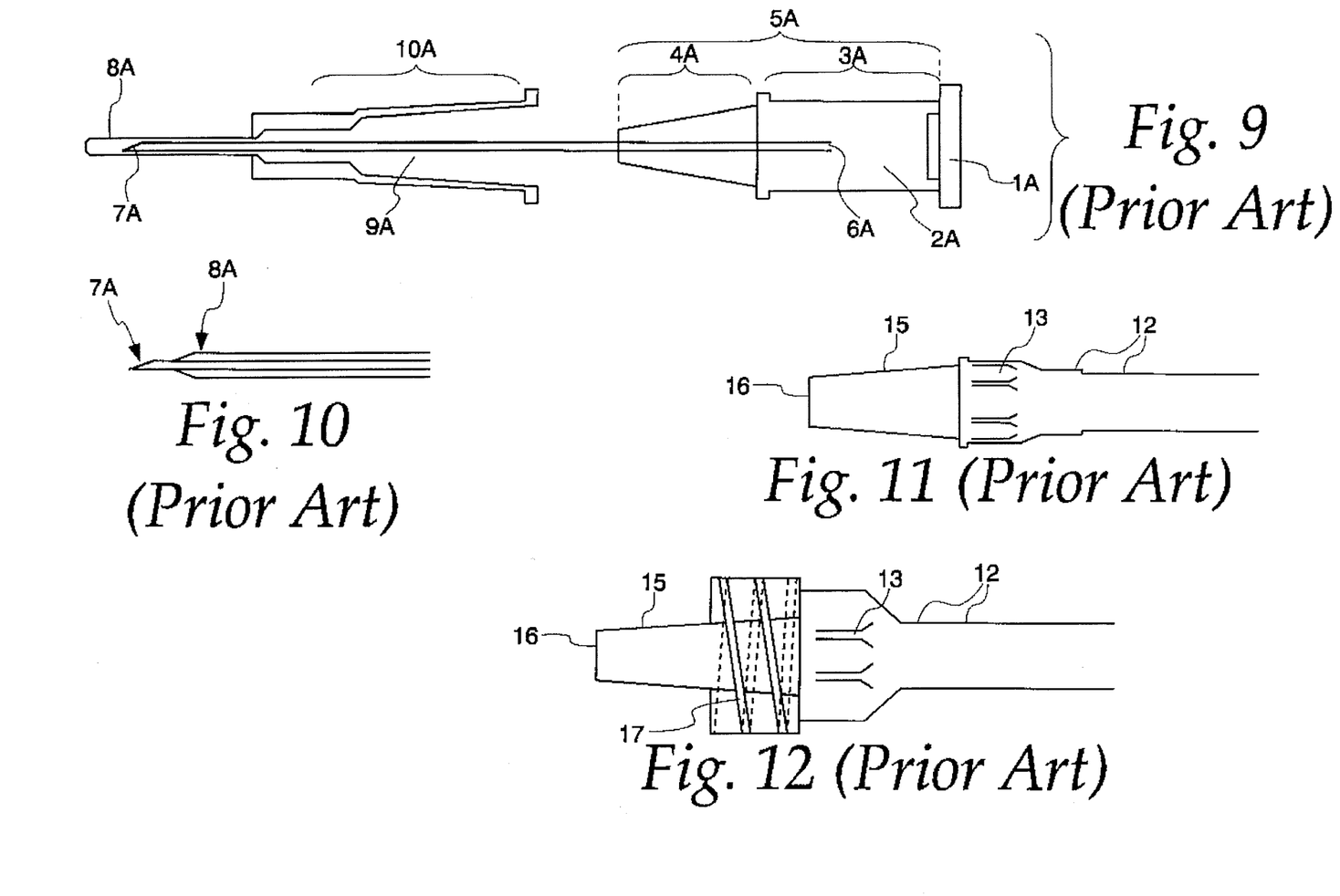
FIG. 9 shows a conventional I.V. catheter with the catheter and needle units separated but aligned with each other.
FIG. 10 shows the position of the distal needle 7A and tapered catheter tip 8A when the catheter and needle units of FIG. 9 are assembled.
FIG. 11 shows a conventional tubing adaptor where 16 is the orifice of tubing adaptor, 13 are finger grips, and 12 is the intravenous tubing.
FIG. 12 shows a tubing adaptor with a locking luer assembly.

Conventional I.V. catheters have been used for years to provide direct access to a patient's veins for administration of intravenous solutions and medications. FIG. 9 shows a currently used design for catheters which includes a catheter-needle complex composed of two main units, the catheter 8A and the needle 7A, each affixed to their hubs 10A and 5A, respectively. The hubs of the two units are connected together in a snug male-female type orientation. During insertion into a patient's vein, the I.V. catheter assembly is held by the rear portion of the needle hub 3A in FIG. 9 with the needle in the "bevel up" position. The needle is advanced (with the two units still joined) through the skin of the patient aiming directly at the vein for entrance into the vein lumen. Entry into the vein will be confirmed when a flashback of blood is seen in the translucent flashback chamber 2A in FIG. 9.

Once the flashback of blood is seen, the needle hub unit 5A is then held stable while the catheter is advanced into the vein by sliding it over the needle in a forward axial motion. (Some recommend slight advancement of the entire unit after the flashback of blood is seen to insure that the needle tip is entirely in the vein lumen before the catheter is advanced.) After the catheter is advanced into the vein, the needle is removed and a tubing adaptor (shown in FIGS. 11 and 12) is connected for administration of fluids. The tubing adaptor has a slightly tapered configuration (see 15 in FIGS. 11 and 12) and is held in place by its very snug fit into the tapered inner channel of the catheter hub 9A in FIG. 9. To provide a more secure connection, some manufacturers have incorporated an external luer lock device on the tubing adaptor (see 17 in FIG. 12).

There are several manufacturers of the above-described I.V. catheter each with their own subtle differences in sizes, shapes, and materials. However, they all conform to the same basic design and are advanced into the vein in similar fashion, namely, by sliding the catheter over the needle in a forward axial motion. In considering all operators placing I.V. catheters and all patients receiving them, one would estimate that at best only 50–60% of the time these catheters are successfully inserted on the first attempt. The other 40–50% of these operations require a second or even a third, fourth, or even fifth attempt, thereby causing excessive pain and contusions to the patient and frustration to the operator.

There are several reasons for the low success rate of insertion of a conventional I.V. catheter on the first attempt. First, the needle may not enter the vein. This is frequently due to very tough skin, "rolling," small or thrombosed veins, or just poor "aim." These difficulties can often be overcome with more thorough evaluation of the vein and puncture site and better technique. A much more frequently encountered problem is when the needle does enter the vein (and a flashback of blood is seen in the flashback chamber), but the catheter, which is made of coated plastic material, will not advance and often buckles or kinks upon sliding forward axially. This situation requires a new catheter and puncture. The resistance to the entry of the catheter usually occurs within the first 1–6 mm of advancement. Several explanations can be given for this problem. First and foremost is the fact that the sharp needle tip is a separate unit from the relatively blunt tapered catheter tip (see needle tip 7A and catheter tip 8A in FIG. 10). The distal catheter must slide axially over the needle through tissues that the sharp needle tip has already traversed. The intervening tissues offer resistance for the catheter tip and shaft. Even when both tips are in the lumen of the vein, the catheter may not advance smoothly because of resistance from the surrounding tissue during the axial sliding motion. A second cause of awkward advancement is related to the "snug" fit design of the male hub component of the needle to the female hub component of the catheter. As the two units are separated when advancing the catheter, there is a subtle recoil of the needle unit caused by the abrupt release of this "snug" fit. The extent of this recoil varies among the different manufactured catheters, depending on the types of material, size of catheter, and the fit. This subtle recoil, which an operator may not even be aware of unless he or she is instructed to consciously take note of it, results in an uneven, non-uniform advancement. In addition, the recoil can cause a minute backward displacement of the needle tip from its desired position in the vein. An additional, but less common, occurrence arises when the puncture site is at or near a vein valve location. Advancement in such a situation may be hindered by resistance from the vein valve.

Manufacturers have attempted to overcome the above deficiencies regarding the use of conventional I.V. catheters by utilizing more advanced, frictionless, and/or less rigid materials. However, although reduced slightly, these problems still exist.

The present invention solves the above-discussed problems by providing catheter assemblies in which rotational movement is integrated into the axial movement of the catheter component during insertion into the patient. In accordance with the invention, forward axial movement of the catheter component can only be achieved by rotation of the catheter component. This integration of the rotational and axial movements of the catheter component overcomes or diminishes the friction forces and other resistance to the penetration of the intervening tissues (e.g., skin, vein walls, etc.) during insertion of the catheter component. The invention also eliminates the recoil phenomenon experienced with conventional catheters during separation and advancement of the catheter components, thus making possible a smoother, more uniform insertion. In addition, the assemblies of the invention permit precise and minute movement control between the catheter and needle components which ensures proper positioning in the vein. The invention results in a more efficient and reliable insertion and a significantly higher percentage of successful placements on the first attempt. Consequently, by using the present invention, there will be fewer puncture attempts, less trauma to the veins, and less contusions. Moreover, the invention standardizes the insertion procedure of catheters which significantly aids in the training of medical personnel.

SUMMARY OF THE INVENTION

The catheter assembly of the present invention comprises (i) a needle component, (ii) a catheter component mounted on the needle component in a manner that permits relative axial movement between the needle component and the catheter component, and (iii) a rotatable screw means for controlling the relative axial movement between the needle component and the catheter component. Preferably, the screw means controls the relative axial movement while simultaneously inducing rotational movement of the catheter component. One means of accomplishing this is for the screw means to comprise a threaded-male member on the hub of the needle component and a corresponding threaded-female member on the hub of the catheter component, or vice versa.

BRIEF DESCRIPTION OF THE FIGURES

FIGS. 1–2 illustrate one embodiment of the present invention.

FIGS. 3–5 illustrate another embodiment of the present invention.

FIGS. 6–8 illustrate still another embodiment of the present invention.

FIGS. 9–12 illustrate conventional I.V. catheters.

DETAILED DESCRIPTION OF THE INVENTION

The following detailed description of the invention sets forth several preferred embodiments. These embodiments are merely illustrative and are not intended to limit the claimed invention. Moreover, although the present disclosure describes the invention primarily in terms of I.V. catheters, its impact goes beyond just I.V. catheters, and may be used on all catheter-type assemblies. Additionally, this disclosure is not intended to be a primer on catheter design and/or manufacture. General assembly, materials of construction, as well as optional or auxiliary aspects or concerns (for example, tube attachments, needle design, lubrication, incorporation and design of needle sheaths, etc.) are known to those skilled in the art.

Figure 1:
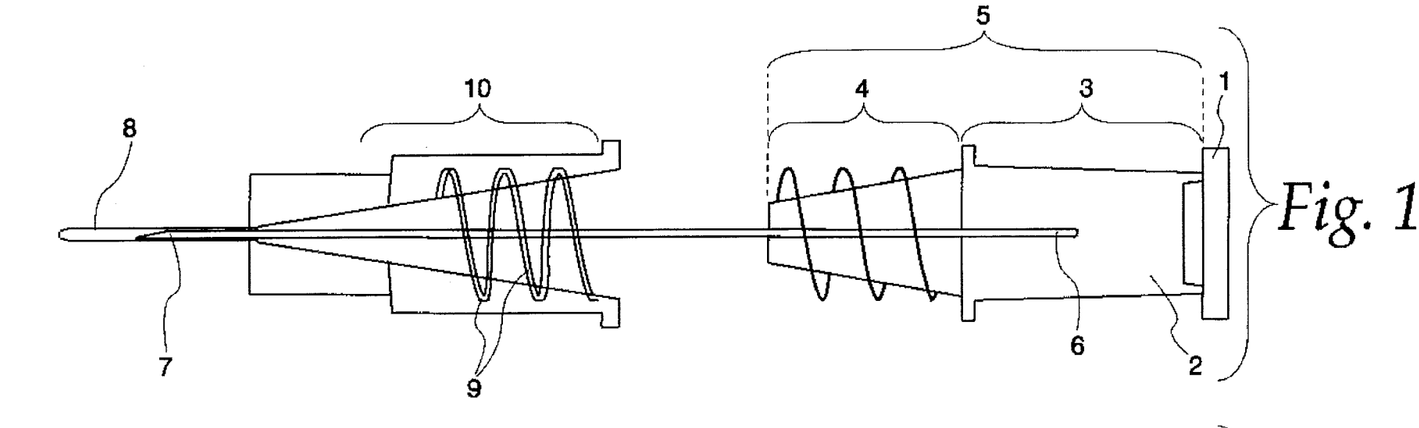
FIG. 1 shows a cross-sectional view of an I.V. catheter in accordance with the invention where the catheter unit 10 and the needle unit 5 are separate from each other but still aligned.
Figure 2:
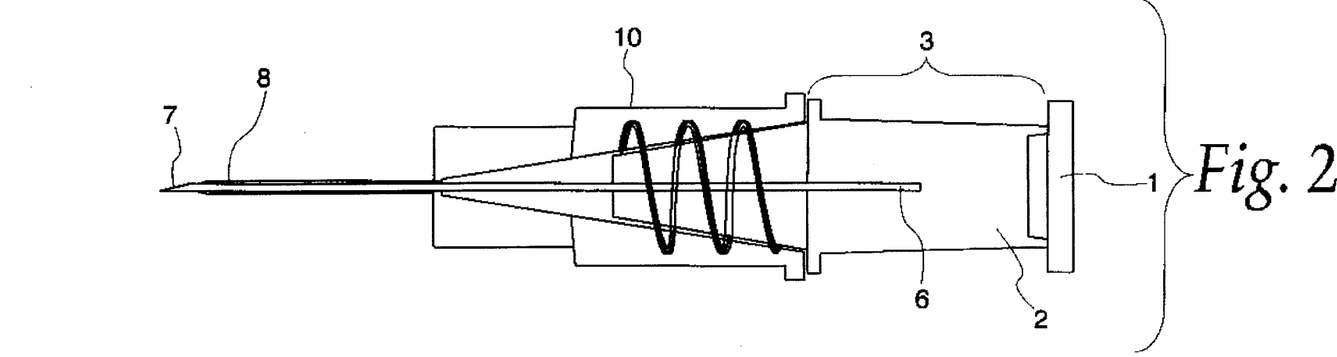
FIG. 2 shows a cross-sectional view of the I.V. catheter of FIG. 1 where the catheter unit 10 and the needle unit 5 are joined.
Figure 3:
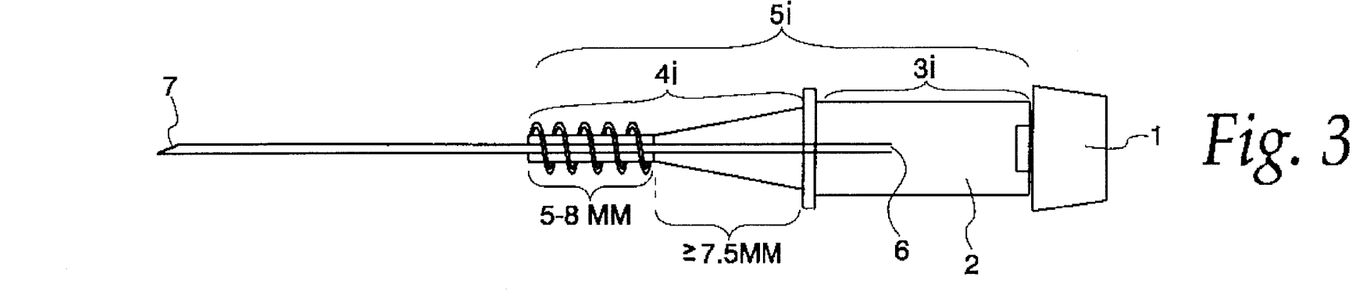
FIG. 3 shows a cross-sectional view of another needle unit.
Figure 4:
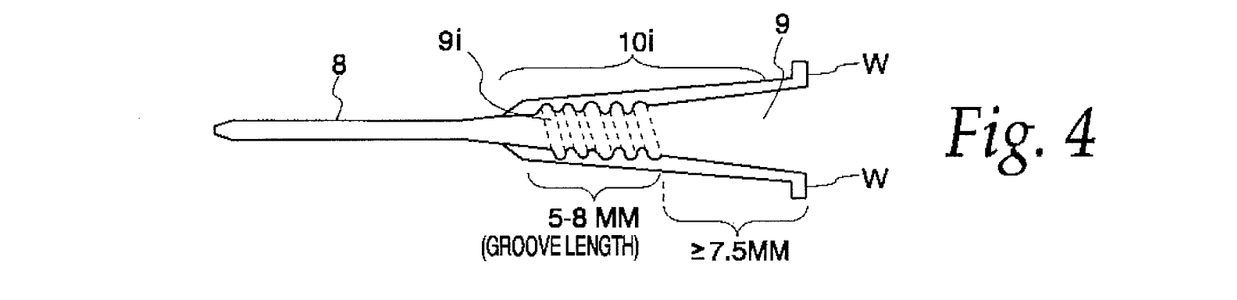
FIG. 4 shows a cross-sectional view of a catheter unit designed for use with the needle unit in FIG. 3.
Figure 5:
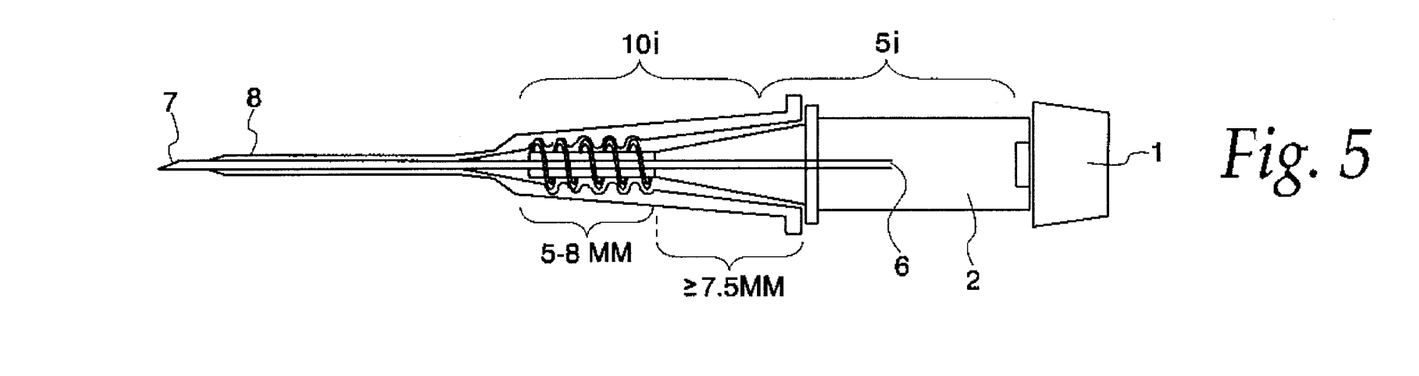
FIG. 5 shows a cross-sectional view of the catheter and needle units in FIGS. 3 and 4 assembled and ready for puncture in accordance with the invention.
Figure 6:
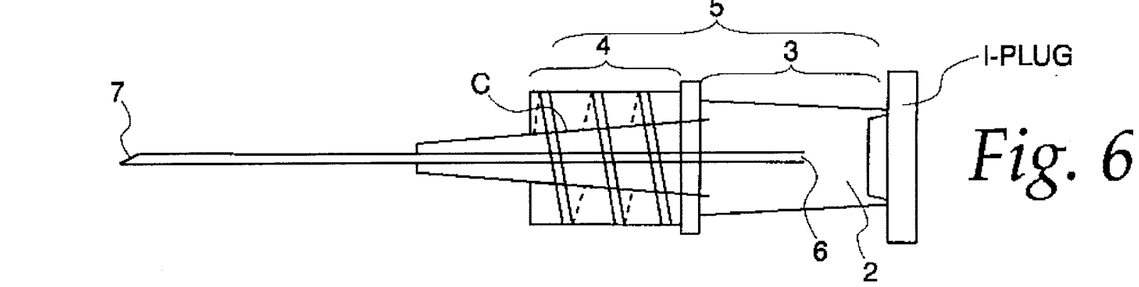
FIG. 6 shows a cross-sectional view of another needle unit.
Figure 7:
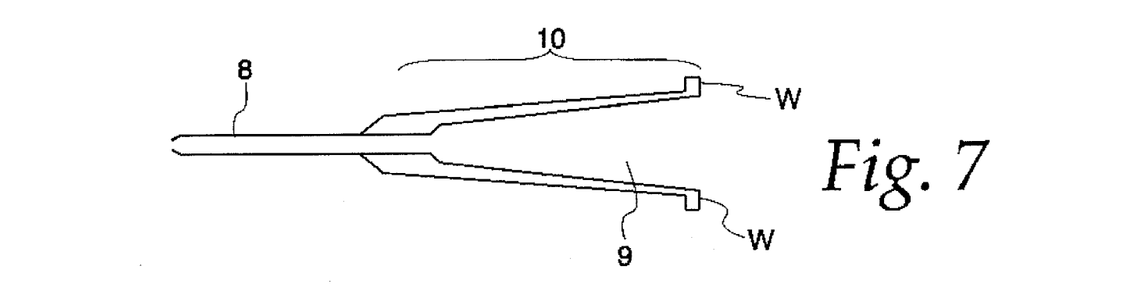
FIG. 7 shows a cross-sectional view of a catheter unit designed for use with the needle unit of FIG. 6.

In basic terms, the invention modifies the needle and catheter components of standard I.V. catheters by the incorporation of a male-female screw thread means. There are several structural designs and variations upon these designs that will achieve the rotary axial motion described in the invention. Several basic embodiments or designs chosen for their relative simplicity will be described. FIGS. 1–2 show a first design, FIGS. 3–5 show a second design, and FIGS. 6–8 a third design in accordance with the invention. FIGS. 9–12 show conventional catheters. Throughout the drawings and specification, similar elements are, when appropriate, identified by the same reference numbers or symbols.

The initial puncture into the vein with the needle unit of the present catheter is essentially the same as for a conventional catheter. However, once blood is seen in the flashback chamber (2 in FIGS. 2, 5, and 8 which is capped by plug 1 or 1A), the catheter component 8 is rotated by the screw means (see FIGS. 2, 5, and 8) in a clockwise fashion, providing a combined rotary-axial motion, and resulting in a smooth, fluid-like advancement. It is generally preferred that the screw means utilizes threads that have an essentially constant diameter over the length of advancement (see FIGS. 1 and 2). In other words, the threads on the hub portion of the needle component 4 in FIG. 1 and the grooves 9 in the female channel of the catheter component maintain an essentially constant diameter even though the hub and channel themselves are tapered. This design allows continuous, secured contact between the two portions at every point during advancement, thus significantly reducing or preventing any "wobbling" effect as seen in the conventional design once the catheter component is displaced 2–3 mm from needle hub. An additional preferred feature of the catheter hub of the present invention (see 10 in FIG. 1) is that it can be made to retain the ability to accept conventional male tubing adaptor (see FIGS. 11 and 12) despite the presence of female screw threads on its inner surface. The screw threads can be designed with a pitch that permits the majority of the inner surface of the catheter hub 15 to be tapered in order to allow a "snug" fit with the universal tubing adaptor which has a slight tapered shape. The catheter hub of the present invention can also accept an external luer lock tubing adaptor (see FIG. 12) in the same manner as conventional catheters.

In another design of the present invention (FIGS. 3–5), the male component 4i of the needle unit 5i has an extended non-tapered portion of the body that has a male threaded pattern (compare 4A in FIG. 9 with 4i in FIG. 3). This extended portion fits into female grooves of catheter channel 9i in FIG. 4 in screw-thread fashion (see FIG. 5). The proximal female channel 9 in FIG. 4 is similar to conventional female channel 9a in FIG. 9. In another design (FIGS. 6–8), the male component 4 of the needle unit 5 has an external cylinder with a female threaded pattern that accommodates the lugs or wings (w in FIG. 7) of the catheter hub 10 in a female-male thread orientation (see FIG. 8). Within the inner cylinder 4 is the male conical component (c in FIG. 6) that has the needle affixed to it. The separation of the hubs of the two components (5i and 10i in FIG. 5; 5 and 10 in FIG. 8) during advancement is a gliding, non-abrupt transition. The friction, resistance forces, and "abrupt recoil" that are experienced with conventional catheters using sliding-type "axial" advancement is diminished or eliminated.

In addition, because the advancement is guided by strategically placed threads, small incremental movements can be easily and precisely controlled. By changing or modifying the pitch of the threads, the rate of movement per complete revolution can be varied and/or controlled over a large range. The bevelled needle tip can be withdrawn slightly and reversed to a down position with counterclockwise motion if its position and its orientation is felt to impede advancement by the operator. These maneuvers are much more difficult with the conventional catheter design.

Figure 8:
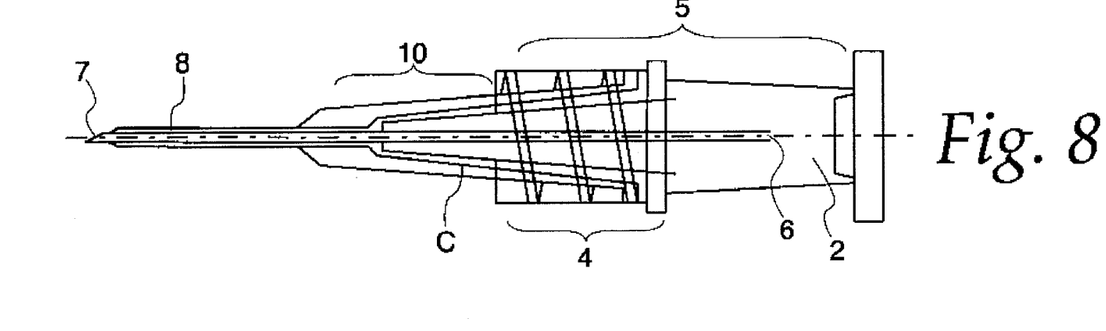
FIG. 8 shows a cross-sectional view of the catheter and needle units in FIGS. 6 and 7 assembled and ready for puncture in accordance with this invention.

The preferred embodiments of the invention illustrated in the figures will now be described in greater detail. In FIGS. 2, 5, and 8, various embodiments of the I.V. catheters of the invention are shown assembled with both needle and catheter components joined (shown separated in FIG. 1, FIGS. 3 and 4, and FIGS. 6 and 7, respectively) and prepared for venous puncture. Generally the designs illustrated in FIGS. 3–5 and FIGS. 6–8 are more preferred since they are essentially in compliance with current guidelines or standards from the International Organization for Standardization (ISO). During insertion the assembly is held by the needle hub 3 or 3i and advanced through the skin aiming at the vein for entrance into the vein lumen. Entry into the vein lumen will be confirmed when blood is seen in the translucent flashback chamber 2 spilling from the proximal end of the needle 6. The description of the placement of the catheter of this invention to this point is similar to a convention I.V. catheter. Once blood is seen in the flashback chamber 2, the needle hub 3 or 3i is then held stable while the catheter hub 10 is turned in a clockwise motion for about ½ to 2 revolutions. This will cause a smooth rotary-axial motion with forward displacement of catheter about 5–8 mm into vein.

The number of revolutions and the distance of advancement will depend on the number of threads and their orientation. By varying the number of threads and their pitch, the smoothness and control of the forward displacement can be varied over a wide range. Preferably, the screw threads are designed so that about ½ to 1½ revolutions will advance the catheter component about 4–9 mm or more preferably about 5–8 mm. The difficulties associated with prior art catheters described previously are usually encountered within the first few millimeters of advancement. Accordingly, designing the screw threads so that ½ to 1½ revolutions produces an advancement of 4–9 mm (or more preferably 5–8 mm) will provide the advantages of the present invention at the time when the most resistance is expected. Suitable dimensions for various components are shown in FIGS. 3–5. Of course, dimensions smaller and larger than those shown can be used and may be preferred in specific applications.

The rotary-axial motion of the inventive catheters results in a uniform, smooth, and fluid-like advancement with significant decrease in resistance forces, "buckling," and uneven displacement as compared with or experienced with the conventional I.V. catheter designs described earlier.

Once the catheter component has advanced approximately 8 mm and is no longer in contact with the screw threads of the needle component, it is then slid over the needle in the conventional manner until it is entirely in the vein. The needle is then removed and a tubing adaptor is connected to the catheter for administration of fluids.

With catheters of the present invention, if after the initial puncture the needle tip is believed to be too distal (caught or through the posterior wall of vein), the beveled tip can be precisely withdrawn by counterclockwise motion on the needle hub while holding the catheter hub stable. The orientation of the bevel tip can be changed to a down position with the same maneuver. This manipulation of the needle tip is difficult with the conventional I.V. catheter design. Another advantage of the design of the present invention is that at every point during forward displacement of the catheter component from the needle component, the two components are in intimate contact with each other because of the preferred essentially constant diameter of the threads. Accordingly, the components stabilize one another during separation and decrease any "wobbling" effect that is experienced with conventional I.V. catheters (see FIGS. 2, 5, and 8). In conventional I.V. catheters, once the catheter is advanced about 3 mm, the catheter component is stabilized only by the needle shaft (see FIG. 9).

All of the above benefits will result in fewer punctures to the patient, less trauma to the vein, and a significantly higher number of successful placements on the first attempt. Even inexperienced operators will be guided by the gauged advancement and have a much more reliable insertion.

The I.V. catheters of this invention preferably have a female channel of the catheter component which is designed to accept conventional tubing adapters (e.g., FIGS. 11 and 12) in the same manner as the female channel of the conventional catheters (9A of FIG. 9). This type of tubing adaptor secures to the catheter component with a "snug fit." Typically, the male hub of the adaptor, 15 in FIGS. 11 and 12, has a slightly larger diameter than the male hub of the needle component, 4A in FIG. 9, in order to achieve a tight fit into the catheter component. If desired, such tubing adapters can be modified with appropriate threads (similar to the screw threads on 4 and 4i in FIGS. 1 and 3) on the male hub 15 so that the tubing adapters can be more securely attached to the corresponding catheter components 10. The threaded female channel of the catheter component of the present invention can also, if desired, accept an external luer lock type tubing adaptor of the type shown in FIG. 12 where 17 is the external luer lock.

It is contemplated that the present invention will offer significant advantages in the use of I.V. catheters on all patients, but will be especially advantageous in the use of I.V. catheters on patients with difficult or small veins, such as elderly patients, pediatric patients, and cancer patients undergoing treatment. In such patients, small imperfect movements of the catheter can have dramatic effects. An additional benefit will be seen in emergency situations where quicker, more efficient and reliable I.V. access is crucial. It is also contemplated that the present invention will offer advantages for any catheter assemblies placed in vessels or any confined delicate anatomical space where precise control of minute movement is critical. These could include catheters for nerve block (epidural) or for arteries for monitoring pressure.

Recently, a trend has developed in the manufacture of needles and I.V. catheters which is concerned with the ability to construct these devices with protective coverings for the needle portion (e.g., sheaths and/or housings) to safeguard the operator from accidentally sticking himself/herself with the needle after its use. It is contemplated that a sheath or a protective housing can easily be incorporated into the catheters of the present invention by those skilled in the art by using the same parameters and technology used for conventional catheters. Such incorporation will, of course, depend upon individual company designs.

Upon reading the subject application, various alternative constructions and designs will become obvious to those That which is claimed is:

1. A catheter assembly comprising (1) a needle component having a needle end, (2) a catheter component mounted on the needle component in a manner that permits relative axial movement between the needle component and the catheter component, and (3) a rotatable screw means for controlling the relative axial movement between the needle component and the catheter component;

wherein the catheter component is mounted on the needle component in a manner to permit rotational movement between the needle component and the catheter component and the screw means controls the relative axial movement by the rotational movement between the needle component and the catheter component;

wherein the screw means comprises a threaded-male member on the needle component and a corresponding threaded-female member on the catheter component; and wherein the needle component has a smooth, tapered conical surface proximal to the threaded-male member and the threaded-male member is closest to the needle end of the needle component and the catheter component has a corresponding smooth, tapered bore to receive the smooth, tapered conical surface of the needle component.

2. A catheter assembly as defined in claim 1, wherein the threaded-male member and the corresponding threaded-female member are about 5 to 8 mm in length and the smooth, tapered conical surface and the smooth, tapered bore are at least 7.5 mm in length.

3. A catheter assembly as defined in claim 1, wherein the threaded-male member has threads of an essentially constant diameter.

4. A catheter assembly as defined in claim 2, wherein the threaded-male member has threads of an essentially constant diameter.

5. A catheter assembly as defined in claim 3, wherein the threads of the threaded-male member has a pitch whereby one-half to three rotations of the catheter component produces an axial movement of about 4 to 9 millimeters.

6. A catheter assembly as defined in claim 1, wherein the catheter component is suitable for administering fluids to a human.

7. A catheter assembly as defined in claim 3, wherein the catheter component is suitable for administering fluids to a human.

8. A catheter assembly as defined in claim 1 further comprising a tubing adaptor for attaching a tube to the catheter component.

9. A catheter assembly as defined in claim 3 further comprising a tubing adaptor for attaching a tube to the catheter component.

10. A catheter assembly as defined in claim 9, wherein the tubing adaptor is modified to include a second threaded-male member which mates with the corresponding threaded-female member of the catheter component.

11. A catheter assembly as defined in claim 1, wherein the needle component further comprises a protective sheath for covering the needle upon removal form the catheter component,, 12. An intravenous catheter assembly comprising (1) a needle component having a needle end, (2) a catheter component mounted on the needle component in a manner which permits relative axial movement and relative rotational movement between the needle component and the catheter component, and (3) a rotatable screw means for controlling the relative axial movement between the needle component and the catheter component by the relative rotational movement between the needle component and the catheter component;

wherein the screw means comprises a threaded-male member on the needle component and a corresponding threaded-female member on the catheter component;

wherein the threads of the threaded-male member has a pitch whereby one-half to three rotations of the catheter component produces an axial movement of about 4 to 9 millimeters; and wherein the needle component has a smooth, tapered conical surface proximal to the threaded-male member and the threaded-male member is closest to the needle end of the needle component and the catheter component has a corresponding smooth, tapered bore to receive the smooth, tapered conical surface of the needle component.

13. An intravenous catheter assembly as defined in claim 12, wherein the threaded-male member and the corresponding threaded-female member are about 5 to 8 mm in length and the smooth, tapered conical surface and the smooth, tapered bore are at least 7.5 mm in length.

14. An intravenous catheter assembly as defined in claim 13, wherein the threaded-male member has threads of an essentially constant diameter.

15. A method for inserting a catheter into a blood vessel or other confined anatomical space of a patient using an assembled catheter assembly having (1) a needle component having a needle end, (2) a catheter component mounted on the needle component in a manner that permits relative axial movement between the needle component and the catheter component, and (3) a rotatable screw means for controlling the relative axial movement between the needle component and the catheter component, said method comprising:

(1) locating the blood vessel or other confined anatomical space of the patient;

(2) inserting the needle component into the blood vessel or other confined anatomical space;

(3) holding the needle component stable while rotating the screw means to smoothly and axially advance the catheter component into the blood vessel or other confined anatomical space to achieve the proper placement of the catheter component within the blood vessel or other anatomical space; and (4) when the catheter component is in the proper placement within the blood vessel or other confined anatomical space, removing the needle component from the catheter assembly in a manner such that the catheter component remains in the proper placement within the blood vessel or other confined anatomical space;

wherein the catheter component is mounted on the needle component in a manner to permit rotational movement between the needle component and the catheter component and the screw means controls the relative axial movement by the rotational movement between the needle component and the catheter component;

wherein the threads of the threaded-male member has a pitch whereby one-half to three rotations of the catheter component produces an axial movement of about 4 to 9 millimeters; and wherein the needle component has a smooth, tapered conical surface proximal to the threaded-male member and the threaded-male member is closest to the needle end of the needle component and the catheter component has a corresponding smooth, tapered bore to receive the smooth, tapered conical surface of the needle component.

16. A method as defined in claim 15, wherein the threaded-male member and the corresponding threaded-female member are about 5 to 8 mm in length and the smooth, tapered conical surface and the smooth, tapered bore are at least 7.5 mm in length.

17. A method as defined in claim 16, wherein the threaded-male member has threads of an essentially constant diameter.

18. A method as defined in claim 15 further comprising attaching a tubing adaptor to the catheter component of step (4).

19. A method as defined in claim 16 further comprising attaching a tubing adaptor to the catheter component of step (4).

20. A catheter assembly comprising (1) a needle component, (2) a catheter component mounted on the needle component in a manner that permits relative axial movement between the needle component and the catheter component, and (3) a rotatable screw means for controlling the relative axial movement between the needle component and the catheter component;

wherein the catheter component is mounted on the needle component in a manner to permit rotational movement between the needle component and the catheter component and the screw means controls the relative axial movement by the rotational movement between the needle component and the catheter component; and wherein the screw means comprises a tapered threaded-male member having threads of an essentially constant diameter on the needle component and a corresponding tapered threaded-female member on the catheter component.

21. A catheter assembly as defined in claim 20, wherein the threads of the threaded-male member has a pitch whereby one-half to three rotations of the catheter component produces an axial movement of about 4 to 9 millimeters.

22. A catheter assembly as defined in claim 20, wherein the catheter assembly is suitable for administrating fluids to a human.

23. A catheter assembly as defined in claim 21, wherein the catheter assembly is suitable for administrating fluids to a human.

24. A catheter assembly as defined in claim 20 further comprising a tubing adaptor for attaching a tube to the catheter component.

25. A catheter assembly as defined in claim 21 further comprising a tubing adaptor for attaching a tube to the catheter component.

26. A catheter assembly as defined in claim 20, wherein the needle component further comprises a protective sheath for covering the needle upon removal from the catheter component.

27. A catheter assembly as defined in claim 21, wherein the needle component further comprises a protective sheath for covering the needle upon removal from the catheter component.

* * * * *

UNITED STATES PATENT AND TRADEMARK OFFICE
CERTIFICATE OF CORRECTION

PATENT NO. : 5,542,930
DATED : August 6, 1996
INVENTOR(S) :
 Israel Schur, M.D.

It is certified that error appears in the above-indentified patent and that said Letters Patent is hereby corrected as shown below:

On the title page: Item

[63] change "Jan. 1, 1995" to --Jan. 6, 1995--.

IN THE CLAIMS:

Claim 11, Column 7, line 63, change "form" to --from--.

Claim 11, Column 7, line 64, change ",," to --.--.

Signed and Sealed this

Twelfth Day of November, 1996

Attest:

BRUCE LEHMAN

*Attesting Officer*       *Commissioner of Patents and Trademarks*